(12) United States Patent
Lee et al.

(10) Patent No.: US 10,172,876 B2
(45) Date of Patent: *Jan. 8, 2019

(54) USE OF GINSENOSIDE M1 FOR TREATING IGA NEPHROPATHY

(71) Applicant: Sheau-Long Lee, Taoyuan (TW)

(72) Inventors: Sheau-Long Lee, Taoyuan (TW); Yu-Chieh Lee, Taoyuan (TW); Ann Chen, Taipei (TW); Kuo-Feng Hua, Yilan County (TW); Shuk-Man Ka, Taipei (TW)

(73) Assignee: Sheau-Long Lee, Taoyuan (TW)

( * ) Notice: Subject to any disclaimer, the term of this patent is extended or adjusted under 35 U.S.C. 154(b) by 9 days.

This patent is subject to a terminal disclaimer.

(21) Appl. No.: 15/315,141

(22) PCT Filed: Nov. 3, 2015

(86) PCT No.: PCT/CN2015/093708
§ 371 (c)(1),
(2) Date: Nov. 30, 2016

(87) PCT Pub. No.: WO2016/070795
PCT Pub. Date: May 12, 2016

(65) Prior Publication Data
US 2018/0214466 A1 Aug. 2, 2018

Related U.S. Application Data

(60) Provisional application No. 62/074,247, filed on Nov. 3, 2014.

(51) Int. Cl.
A61K 31/704 (2006.01)
A61K 45/06 (2006.01)
A61P 13/12 (2006.01)
A61K 9/00 (2006.01)

(52) U.S. Cl.
CPC .......... *A61K 31/704* (2013.01); *A61K 9/0019* (2013.01); *A61K 45/06* (2013.01); *A61P 13/12* (2018.01)

(58) Field of Classification Search
None
See application file for complete search history.

(56) References Cited

U.S. PATENT DOCUMENTS 8,673,851 B2 * 3/2014 Rastaldi ............... A61K 31/165
424/198.1
9,844,560 B2 * 12/2017 Lee ....................... A61K 31/704

FOREIGN PATENT DOCUMENTS

WO  WO-2005102326 A2 * 11/2005 ........... A61K 31/404

* cited by examiner

*Primary Examiner* — Traviss C McIntosh, III
(74) *Attorney, Agent, or Firm* — WPAT, PC

(57) ABSTRACT

The present invention provides a method of treating a subject afflicted with IgA nephropathy (IgAN) comprising administering to the subject an amount of ginsenoside M1 effective to treat the subject.

6 Claims, 14 Drawing Sheets
Specification includes a Sequence Listing.

(A)

(B)

USE OF GINSENOSIDE M1 FOR TREATING IGA NEPHROPATHY

RELATED APPLICATION

This application claims priority to U.S. Provisional Application No. 62/074,247, filed on Nov. 3, 2014, the content of which is hereby incorporated by reference in its entirety.

FIELD OF THE INVENTION

The present invention relates to a new use of ginsenoside M1 for treating IgA nephropathy (IgAN).

BACKGROUND OF THE INVENTION

IgA nephropathy (IgAN) is the most common form of glomerulonephritis (GN) worldwide. The onset of IgAN may be associated with an upper respiratory tract infection [1,2]. Frequently, C3 and other classes of immunoglobulin deposits are detected in a pattern similar to the IgA. The most common histopathologic alterations include focal or diffuse expansion of mesangial regions with proliferative cells and extracellular matrix [3]. Additionally, a wide variety of lesions may be seen in patients with more severe lesions, including diffuse endocapillary proliferation, segmental sclerosis, segmental necrosis, and cellular crescent formation [4,5]. And reactive oxygen species (ROS) have been reported to play a major pathogenic role in the development of a wide range of human and experimental glomerular disorders, including IgAN [6-8]. Although IgAN is considered an immune complex disease resulting from IgA-immune complex (IgA-IC) glomerular damage, the cause of the disease and the pathogenic mechanisms that propagate this disease are unknown.

Although glucocorticoid steroids have been used to treat some of IgAN patients, their efficacy in preserving the deterioration of renal function in IgAN remains largely unclear, and the long-term use of these drugs can cause severe adverse side effects because of potential uncontrollable immunosuppressive effects [9-11].

Ginsenosides, the main active ingredients of ginseng, are known to have a variety of pharmacological activities, e.g. antitumor, antidiabetic, antifatique, antiallergic and antioxidant activities. Ginsenosides share a basic structure, composed of gonane steroid nucleus having 17 carbon atoms arranged in four rings. Ginsenosides are metalized in the body, and a number of recent studies suggest that ginsenoside metabolites, rather than naturally occurring ginsenosides, are readily absorbed in the body and act as the active components. Among them, ginsenoside M1 is known as one metabolite of protopanaxadiol-type ginsenosides via the gypenoside pathway by human gut bacteria. Until now, no prior art references report the effect of ginsenoside M1 in treatment of IgAN.

BRIEF SUMMARY OF THE INVENTION

In the present invention, it is unexpected found that ginsenoside M1 is effective in alleviating the symptoms of IgA nephropathy (IgAN). Therefore, the present invention provides a new approach for treatment of IgAN in a subject.

In particular, the present invention provides a method for treating a subject afflicted with IgAN comprising administering to the subject ginsenoside M1 in an amount effective to treat the subject.

Specifically, the method of the present invention is effective in reducing one or more symptoms of IgAN in the subject, selected from the group consisting of (1) in the glomerulus: intrinsic cell proliferation including mesangial cell proliferation, crescent formation, neutrophil infiltration and segmental sclerosis; and (2) in the tubulointerstitial compartment: interstitial (especially peri-glomerular) mononuclear leukocyte inflammation, fibrosis, and tubular atrophy with proteinaceous casts, in the subject. Also, the method of the present invention is effective in reducing proteinuria or hematuria or lowering serum urea nitrogen level or serum creatinine level in the subject.

In some embodiments, ginsenoside M1 is administered by parenteral or enteral route.

In some embodiments, ginsenoside M1 is administered in combination with one or more therapeutic agents for treating IgAN known in the art, including but not limited to corticosteroids (such as prednisolone), non-steroidal anti-inflammatory drugs (NSAIDs), cytotoxic drugs (such as cyclophosphamide, chlorambucil, and azathioprine), immunosuppressants (such as cyclosporine and Mycophenolate Mofetil), and vasodilators (such as angiotensin-converting-enzyme inhibitors (ACE inhibitors).

The present invention also provides use of ginsenoside M1 in manufacturing a medicament for treatment of IgAN in a subject in need.

The details of one or more embodiments of the invention are set forth in the description below. Other features or advantages of the present invention will be apparent from the following detailed description of several embodiments, and also from the appending claims.

BRIEF DESCRIPTION OF THE DRAWINGS

For the purpose of illustrating the invention, there are shown in the drawings embodiments. It should be understood, however, that the invention is not limited to the preferred embodiments shown. In the drawings.

DETAILED DESCRIPTION OF THE INVENTION

Figure 1:
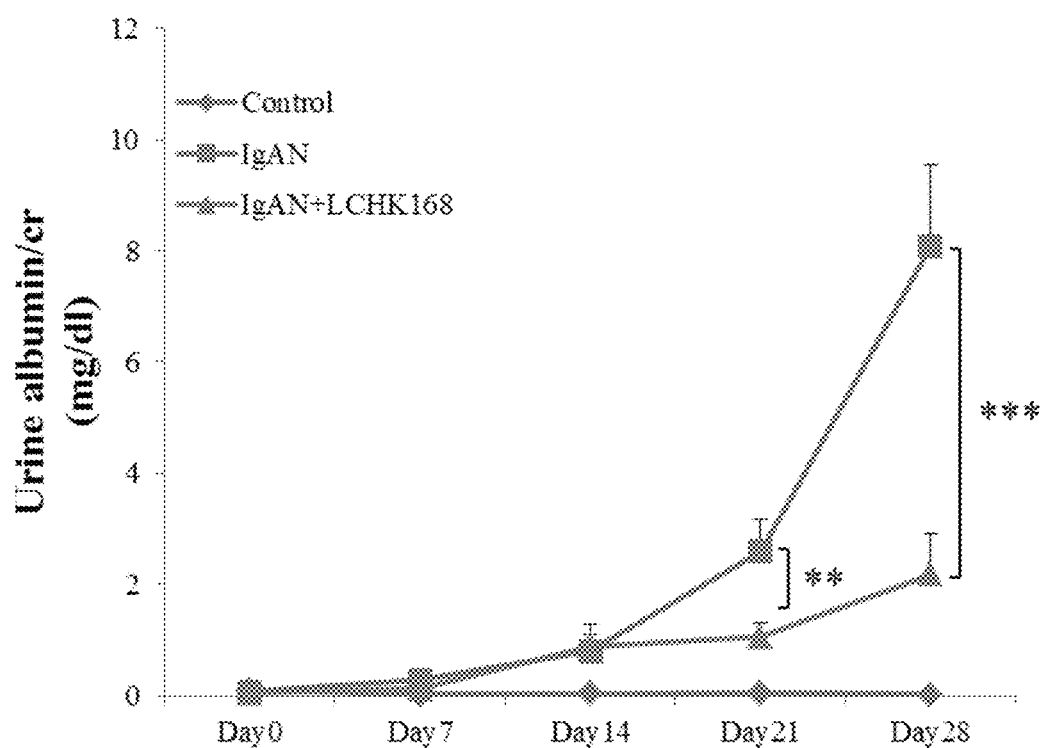
FIG. 1 shows the effects of LCHK168 on urine protein. Time-course studies of urine protein levels (ratio of urine protein to creatinine [Cr]). $p<0.01$, *$p<0.005$.

Unless defined otherwise, all technical and scientific terms used herein have the meaning commonly understood by a person skilled in the art to which this invention belongs. As used herein, the following terms have the meanings ascribed to them unless specified otherwise.

The articles "a" and "an" are used herein to refer to one or more than one (i.e., at least one) of the grammatical object of the article. By way of example, "an element" means one element or more than one element.

In the present invention, it is unexpectedly found that ginsenoside M1 can prevent development of IgAN by administering it to IgAN mice. In particular, it is found that animals with IgAN present various symptoms including (1) in the glomerulus: intrinsic cell proliferation including mesangial cell proliferation, crescent formation, neutrophil infiltration and segmental sclerosis; and (2) in the tubulointerstitial compartment: interstitial (especially peri-glomerular) mononuclear leukocyte inflammation, fibrosis, and tubular atrophy with proteinaceous casts, or proteinuria or hematuria, or elevated serum urea nitrogen level or serum creatinine level.

Therefore, the present invention provides a method for treating a subject afflicted with IgAN comprising administering to the subject ginsenoside M1 in an amount effective to treat the subject. The present invention also provides use of ginsenoside M1 for manufacturing a medicament for treating IgAN in a subject in need thereof.

The method of the invention is effective in improving any one of these symptoms in patients with IgAN.

Ginsenoside M1, 20-O-β-D-glucopyranosyl-20(S)-protopanaxadiol, is one of saponin metabolites known in the art. The chemical structure of ginsenoside M1 is as follows:

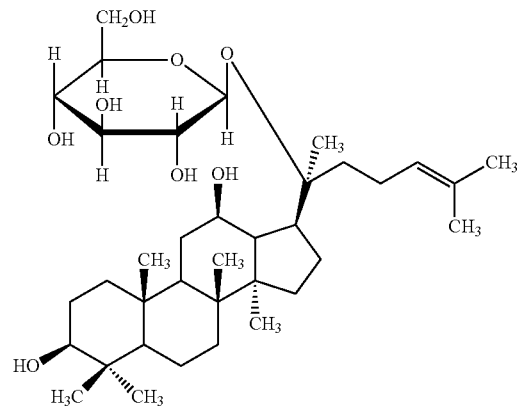

Ginsenoside M1 is known as one metabolite of protopanaxadiol-type ginsenosides via the gypenoside pathway by human gut bacteria. Ginsenoside M1 can be found in blood or urine after intake. Ginsenoside M1 may be prepared from ginseng plants through fungi fermentation by methods known in the art, such as Taiwan Patent Application No. 094116005 (1280982) and U.S. Pat. No. 7,932,057, the entire content of which is incorporated herein by reference. In certain embodiments, the ginseng plants for preparing the ginsenoside M1 include Araliaceae family, *Panax* genus, e.g. *P. ginseng* and *P. pseudo*-ginseng (also named Sanqi). In general, the method of preparation of ginsenoside M1 includes the steps of (a) providing powder of ginseng plant materials (e.g. leaves or stems); (b) providing a fungus for fermenting the ginseng plant materials, wherein the fermentation temperature is ranged from 20-50° C., the fermentation humidity is ranged from 70-100%, the pH value is ranged from 4.0-6.0, and the fermentation period is ranged from 5-15 days; (c) extracting and collecting the fermentation products; and (d) isolating 20-O-β-D-glucopyranosyl-20(S)-protopanaxadiol from the fermentation products.

When ginsenoside M1 is described as "isolated" or "purified" in the present invention, it should be understood as not absolutely isolated or purified, but relatively isolated or purified. For example, purified ginsenoside M1 refers to one that is more purified compared to its naturally existing form. In one embodiment, a preparation comprising purified ginsenoside M1 may comprise ginsenoside M1 in an amount of more than 50%, more than 60%, more than 70%, more than 80%, more than 90%, or 100% (w/w) of the total preparation. It should be understood that when a certain number was used herein to show a ratio or dosage, said number generally includes that within the range of 10% more and less, or more specifically, the scope of 5% more and less than the number.

The term "individual" or "subject" used herein includes human and non-human animals such as companion animals (such as dogs, cats and the like), farm animals (such as cows, sheep, pigs, horses and the like), or laboratory animals (such as rats, mice, guinea pigs and the like). Specifically, the subject is one afflicted with IgAN.

The term "treating" as used herein refers to the application or administration of a composition including one or more active agents to a subject afflicted with a disorder, a symptom or conditions of the disorder, or a progression of the disorder, with the purpose to cure, heal, alleviate, relieve, alter, remedy, ameliorate, improve, or affect the disorder, the symptoms or conditions of the disorder, the disabilities induced by the disorder, or the progression of the disorder.

The term "therapeutically effective amount" used herein refers to the amount of an active ingredient to confer a therapeutic effect in a treated subject. For example, an effective amount for treating IgAN is an amount that can prohibit, improve, alleviate or reduce one or more symptoms or conditions such as (1) in the glomerulus: intrinsic cell proliferation including mesangial cell proliferation, crescent formation, neutrophil infiltration and segmental sclerosis; and (2) in the tubulointerstitial compartment: interstitial (especially peri-glomerular) mononuclear leukocyte inflammation, fibrosis, and tubular atrophy with proteinaceous casts, or proteinuria or hematuria, or elevated serum urea nitrogen level or serum creatinine level, in a subject having IgAN. The symptoms may be determined and evaluated using methods known in the art based on various disease progress-related indexes, for example by analyzing the amount of urine protein, blood urea nitrogen or serum creatinine, or by analyzing renal sections. The therapeutically effective amount may change depending on various reasons, such as administration route and frequency, body weight and species of the individual receiving said pharmaceutical, and purpose of administration. Persons skilled in the art may determine the dosage in each case based on the disclosure herein, established methods, and their own experience. For example, in certain embodiments, the oral dosage of ginsenoside M1 used in the present invention is 10 to 1,000 mg/kg daily. In some examples, the oral the oral dosage of ginsenoside M1 used in the present invention is 100 to 300 mg/kg daily, 50 to 150 mg/kg daily, 25 to 100 mg/kg daily, 10 to 50 mg/kg daily, or 5 to 30 mg/kg daily. In addition, in some embodiments of the invention, ginsenoside M1 is administered periodically for a certain period of time, for example, daily administration for at least 15 days, one month or two months or longer.

According to the present invention, ginsenoside M1 may be used as an active ingredient for treating IgAN. In one embodiment, a therapeutically effective amount of the active ingredient may be formulated with a pharmaceutically acceptable carrier into a pharmaceutical composition of an appropriate form for the purpose of delivery and absorption. Depending on the mode of administration, the pharmaceutical composition of the present invention preferably comprises about 0.1% by weight to about 100% by weight of the active ingredient, wherein the percentage by weight is calculated based on the weight of the whole composition.

As used herein, "pharmaceutically acceptable" means that the carrier is compatible with the active ingredient in the composition, and preferably can stabilize said active ingredient and is safe to the individual receiving the treatment. Said carrier may be a diluent, vehicle, excipient, or matrix to the active ingredient. Some examples of appropriate excipients include lactose, dextrose, sucrose, sorbose, mannose, starch, Arabic gum, calcium phosphate, alginates, tragacanth gum, gelatin, calcium silicate, microcrystalline cellulose, polyvinyl pyrrolidone, cellulose, sterilized water, syrup, and methylcellulose. The composition may additionally comprise lubricants, such as talc, magnesium stearate, and mineral oil; wetting agents; emulsifying and suspending agents; preservatives, such as methyl and propyl hydroxybenzoates; sweeteners; and flavoring agents. The composition of the present invention can provide the effect of rapid, continued, or delayed release of the active ingredient after administration to the patient.

According to the present invention, the form of said composition may be tablets, pills, powder, lozenges, packets, troches, elixers, suspensions, lotions, solutions, syrups, soft and hard gelatin capsules, suppositories, sterilized injection fluid, and packaged powder.

The composition of the present invention may be delivered via any physiologically acceptable route, such as oral, parenteral (such as intramuscular, intravenous, subcutaneous, and intraperitoneal), transdermal, suppository, and intranasal methods. Regarding parenteral administration, it is preferably used in the form of a sterile water solution, which may comprise other substances, such as salts or glucose sufficient to make the solution isotonic to blood. The water solution may be appropriately buffered (preferably with a pH value of 3 to 9) as needed. Preparation of an appropriate parenteral composition under sterile conditions may be accomplished with standard pharmacological techniques well known to persons skilled in the art, and no extra creative labor is required.

According to the present invention, ginsenoside M1 or compositions comprising ginsenoside M1 as the active ingredient may be used in treating individuals with IgAN. Specifically, ginsenoside M1 or compositions comprising ginsenoside M1 as the active ingredient may be administered to individuals with IgAN or individuals with the risk of acquiring IgAN so as to prevent occurrence of the disease or improve the symptoms or delay deterioration of the symptoms.

In addition, according to the present invention, ginsenoside M1 or compositions comprising ginsenoside M1 as the active ingredient may be used in combination with existing therapeutic methods or medicaments, such as pharmaceutical treatment, including but not limited to corticosteroids (such as prednisolone), non-steroidal anti-inflammatory drugs (NSAIDs), cytotoxic drugs (such as cyclophosphamide, chlorambucil, and azathioprine), immunosuppressants (such as cyclosporine and Mycophenolate Mofetil), and vasodilators (such as angiotensin-converting-enzyme inhibitors (ACE inhibitors)). In one embodiment, the medicament or therapeutic method used in combination may be used simultaneously (parallel) or sequentially. When medicaments are used in combination, the medicaments may be mixed in the same formula or put in different formulas separately, such as separate capsules, pills, tablets, and injections.

The present invention is further illustrated by the following examples, which are provided for the purpose of demonstration rather than limitation.

Example

1. Materials and Methods 1.1 Animal Model and Experimental Protocol

B-cell-deficient mice were obtained from the Academia Sinica (Professor John T. Kung, Institute of Molecular Biology, Taipei, Taiwan) and maintained at the animal center of the National Defense Medical Center (Taipei, Taiwan). IgAN was induced by daily injection of purified IgA anti-phosphorylcholine antibodies and pneumococcal C-polysaccharide antigen (PnC) [14]. All animal experiments were performed with the approval of the Institutional Animal Care and Use Committee of the National Defense Medical Center and complied with the NIH Guide for the Care and Use of Laboratory Animals.

1.2 Ginsenoside M1

Ginsenoside M1, 20-O-β-D-glucopyranosyl-20(S)-protopariaxadiol (named LCHK168 below), was prepared by methods known in the art, such as those described in Taiwan Patent Application No. 094116005 (1280982) and U.S. Pat. No. 7,932,057. The mice were treated daily with 60 mg/kg LCHK168 or with the vehicle, by oral gavage throughout the experiment, the first dose being given 2 day before disease induction.

1.3 Analysis of Urine Protein and Renal Function

Body weight was measured weekly. Urine samples were collected in metabolic cages weekly and urine protein was determined. Serum samples were collected on days 14 and 28 to measure serum levels of blood urea nitrogen (BUN) and creatinine (Cr). For renal histopathology, the tissues were fixed in 10% buffered formalin and embedded in paraffin, and then sections (3 μm) were prepared and stained with hematoxylin and eosin (H&E). The percentage of glomeruli showing proliferation, neutrophil infiltration, sclerosis, or periglomerular inflammation was determined by counting 50 randomly sampled glomeruli by light microscopy at a magnification of 400×.

1.4 Pathologic Evaluation

For IHC, formalin-fixed and paraffin-embedded tissue sections or frozen sections were incubated overnight at 4. C with anti-bodies against CD3, F4/80, CD4, CD8, CD11c, Collagen IV, diluted in DAKO antibody dilution buffer (DAKO), and then for 1 h at room temperature with horseradish peroxidase (HRP)-conjugated second antibodies (DAKO) in the same buffer; in the case of the HRP-conjugated antibodies, DAB (DAKO) was also added. Hematoxylin was used to counterstain nuclei. Positive cells was counted at a magnification of 400× in 20 consecutive glomeruli or in 20 randomly selected fields of the tubule interstitial compartment in the cortical area by Pax-It quantitative image analysis software.

1.5 Measurement of Reactive Oxygen Species (ROS)

To measure ROS levels in renal tissue, the samples were incubated at room temperature with Krebs-Hepes buffer containing 1.25 mM lucigenin (Sigma, St. Louis, Mo., USA) as substrate, and luminescence counts were measured in duplicate at 15-s intervals on a multilabel microplate reader (Hidex). ROS activity was expressed as relative luminescence units (RLU) per 15 minutes per milligram of organ dry weight (i.e., RLU/15 min/mg) or as RLU/15 min/ml.

1.6 Flow Cytometry

Splenocytes from the mice were treated with Tris-buffered ammonium chloride to eliminate erythrocytes, washed and resuspended in RPMI1640 medium supplemented with 10% fetal calf serum, Hepes buffer, L-glutamine, and penicillin/streptomycin. The cells were triple-stained for activated T cell subtypes using FITC-conjugatedanti-mouse CD44, phycoerythrin-conjugated anti-mouse CD62 antibodies, and allophycocyanin-conjugated anti-mouse CD4 and analyzed using a FACSCalibur.

Dendritic cells (DCs) maturation was determined by the upregulation of costimulatory molecule expression. Cells were treated with IgA-IC, LCHK168 (1, 2 μM) and stained with mAbs specific for mouse CD40, CD80, and CD86 and then analyzed by flow cytometry.

1.7 Real-Time Reverse Transcription-Polymerase Chain Reaction (RT-PCR)

Renal cortex RNA was extracted using TRIzol reagent according to the manufacturer's instructions, and RT-PCR was used to measure TLR2 gene expression. The following primers were used: for TLR2, 5'-GTCTCT GCGACCTA-GAAGTGGA-3' (SEQ ID NO: 1) and 5'-CG-GAGGGAATAGAGGTGAAAGA-3' (SEQ ID NO: 2) and for GAPDH, 5'-TCCGCCCCTTCTGCCGATG-3' (SEQ ID NO: 3) and 5'-ACGGAAGGCCATGCCAGTGA-3' (SEQ ID NO: 4). Real-time quantification was performed using a Applied Biosystems according to the manufacturer's instructions. Amplifications were normalized to the values for GAPDH using the $2^{-\Delta C_T}$ method.

1.8 Western Blot Analysis

Each protein sample was run on a 8% SDS-PAGE gel and the proteins were electro blotted on to a polyvinylidene difluoride membrane, which was then incubated for 1 h at room temperature in blocking buffer (Tris-buffered saline containing 5% skim milk) and then overnight at 4° C. with rabbit antibodies against NLRP3 or β-actin. After being washed, the membrane was incubated for 1 h at room temperature with HRP-conjugated goat anti-rabbit IgG antibody in the same buffer; then bound antibody was detected using UVP Biospectrum.

1.9 Statistical Analysis

Values are means±SE. Comparison between two groups was performed using Student's t-test. P value >0.05 was considered statistically significant.

2. Results 2.1 Significant Reduction of Proteinuria and Hematuria and Protection of Renal Function in IgA Mice by Ginsenoside M1

Figure 2:
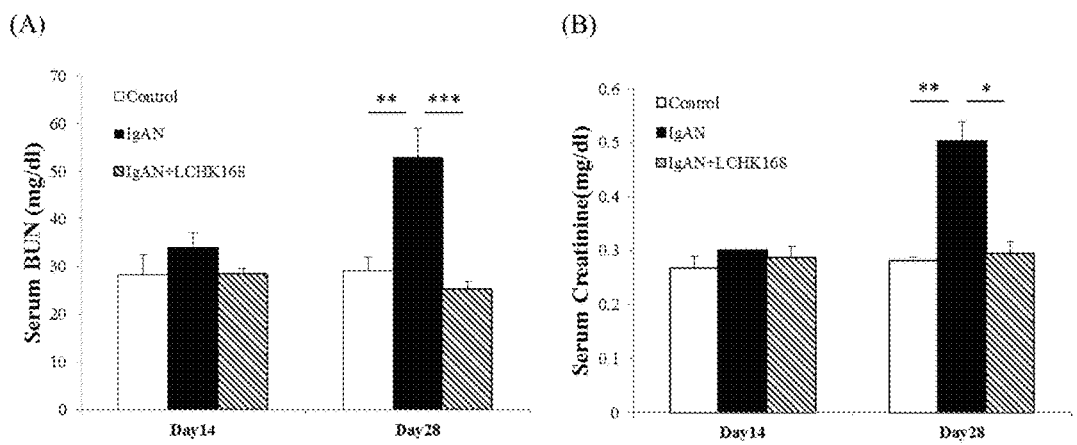
FIG. 2 shows the treatment with LCHK168 improves renal function in mice model of IgA nephropathy (IgAN). (A) Serum blood urea nitrogen (BUN) levels. (B) Serum creatinine (Cr) levels. *$p<0.05$, $p<0.01$, *$p<0.005$.

The disease control mice, i.e., IgAN mice treated with vehicle (control IgAN mice), showed increased urine protein levels from day 14 of disease induction and these continued to rise up to the end of the study on day 28 (FIG. 1). This effect was markedly inhibited by LCHK168 (IgAN+LCHK168), although the mice still showed mild proteinuria compared to normal untreated controls. In addition, compared to disease control mice, which showed significantly increased serum levels of BUN (FIG. 2A) and Cr (FIG. 2B) on day 28, IgAN+LCHK168 mice showed much better renal function. On day 14, there was no significant difference in serum levels of BUN and Cr between disease control, IgAN+LCHK168, and normal control mice.

2.2 Prevention of Severe Renal Histopathologic Features in Mice Treated with LCHK168

Figure 3:
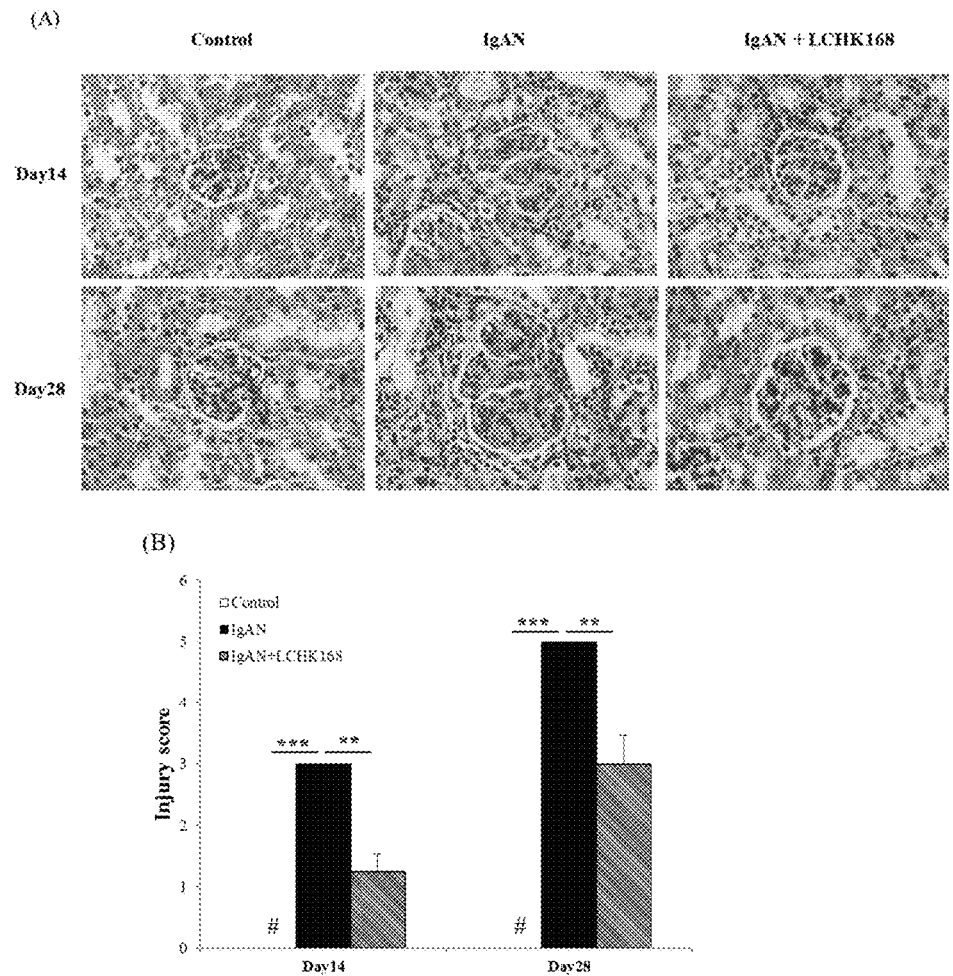
FIG. 3 shows the treatment with LCHK168 ameliorates the severe renal histopathologic features in mice model of IgA nephropathy (IgAN). (A) Kidney histopathological evaluation by H&E staining. Original magnification, 400×. (B) Scoring of the percentage of glomeruli affected by the indicated parameter. $p<0.01$, *$p<0.005$, #Not detectable.

As shown in FIG. 3, on day 28, disease control IgAN mice showed diffuse proliferation associated with focal, but typical crescents; segmental sclerosis and/or neutrophil infiltration in the glomerulus, intense periglomerular mononuclear leukocyte infiltration, and scattered tubular atrophy associated with protein casts in the tubulointerstitial compartment, but this renal lesion was significantly inhibited by the administration of LCHK168.

2.3 Inhibition of Renal Inflammation and Fibrosis in Mice Treated with LCHK168

Figure 4:
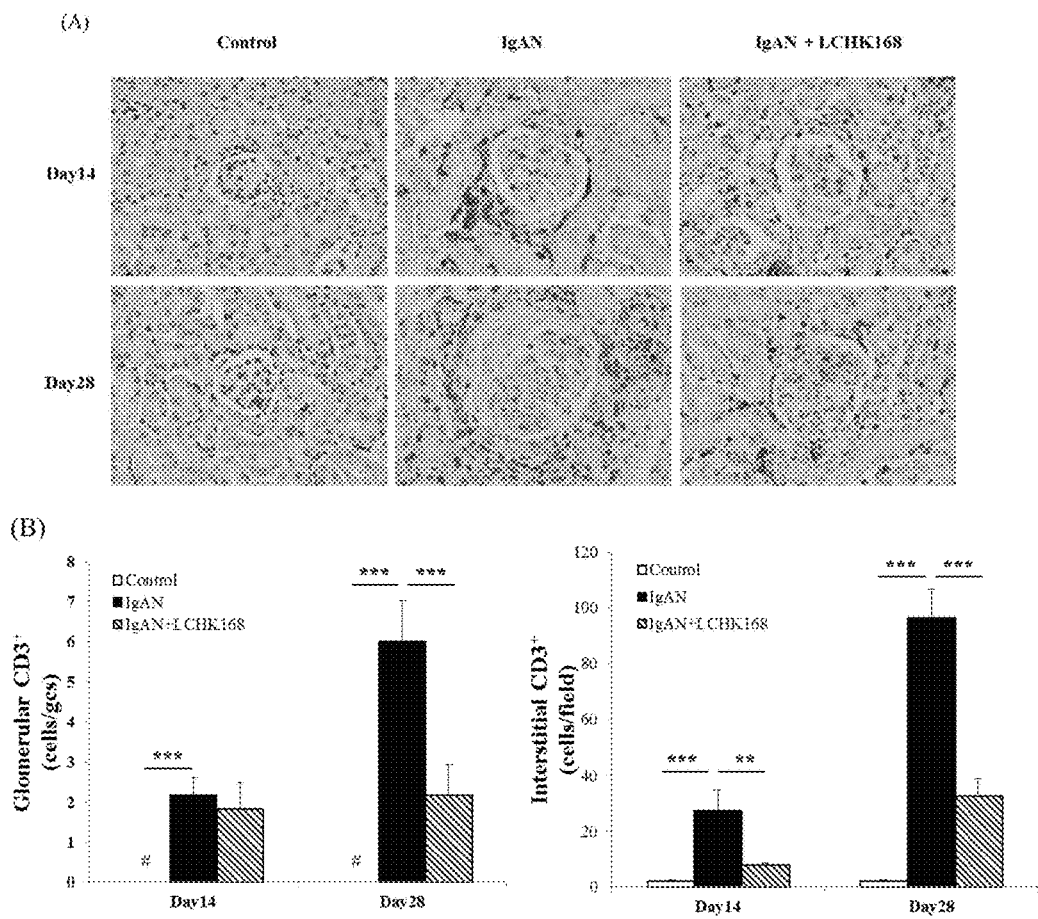
FIG. 4 shows the effects of LCHK168 on T cell infiltration. In mice with IgAN treated with LCHK168, as compared with vehicle-treated disease controls and normal controls. Staining of renal tissues for (A) CD3+ T cells. (B) Scoring of stained cells in the glomerulus and periglomeruli. Original magnification, 400×. $p<0.01$, *$p<0.005$, Not detectable.
Figure 5:
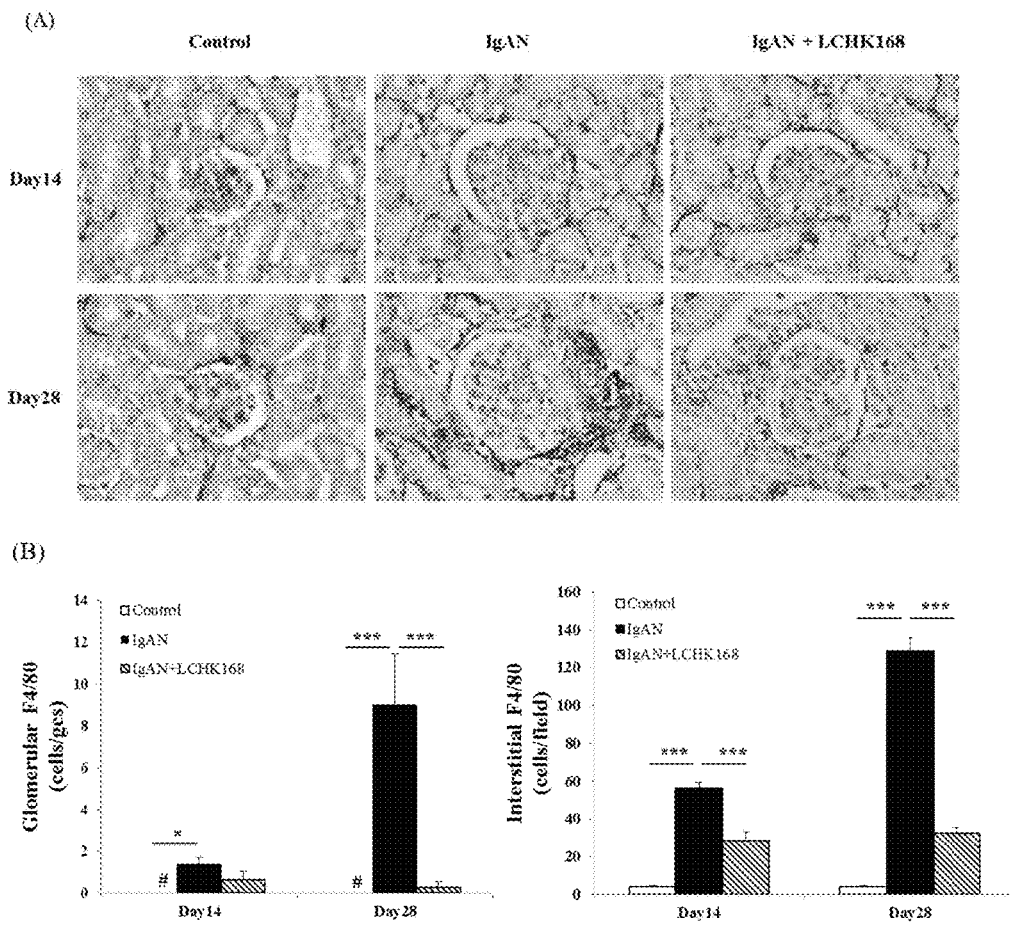
FIG. 5 shows the effects of LCHK168 on monocyte/macrophage infiltration. In mice with IgAN treated with LCHK168, as compared with vehicle-treated disease controls and normal controls. Staining of renal tissues for (A) F4/80$^+$ monocytes/macrophages. (B) Scoring of stained cells in the glomerulus and periglomeruli. Original magnification, 400×. *$p<0.05$, ***$p<0.005$, Not detectable.
Figure 6:
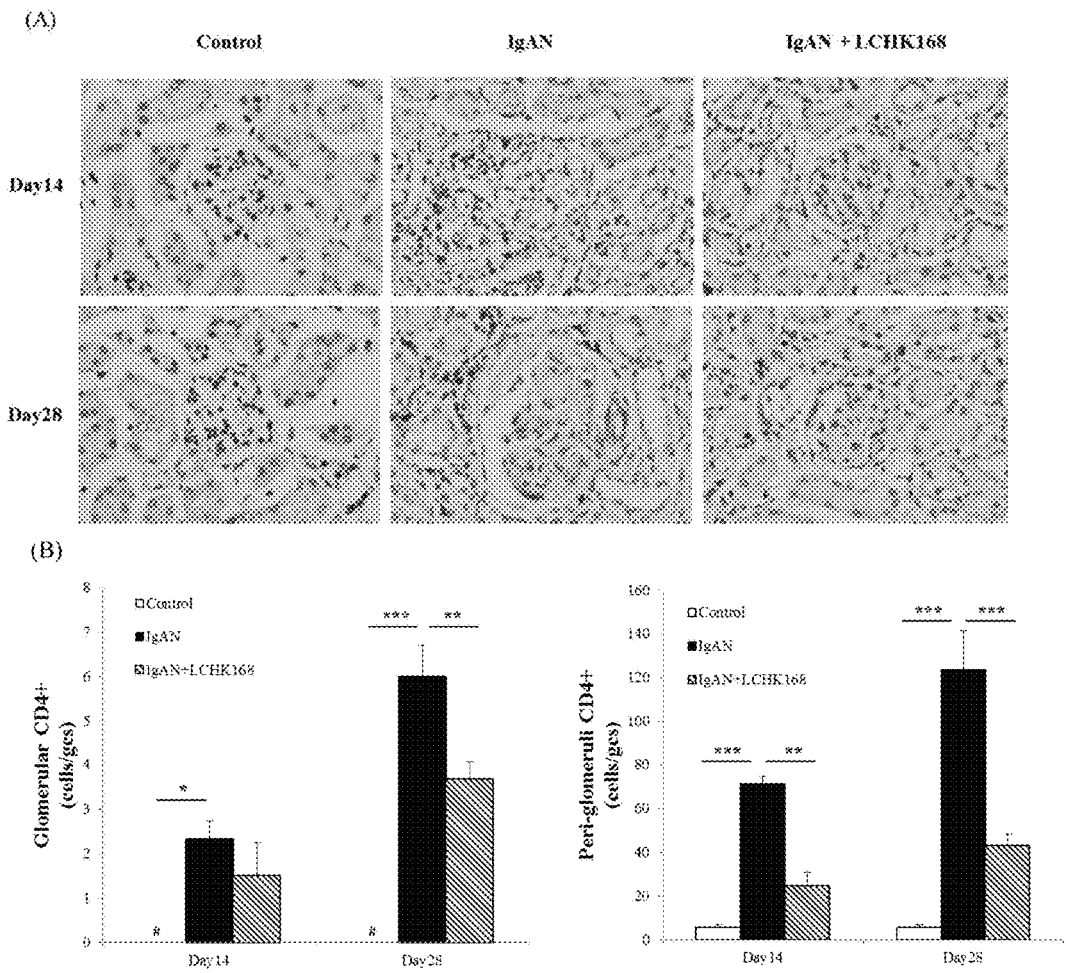
FIG. 6 shows the effects of LCHK168 on Th cell infiltration. In mice with IgAN treated with LCHK168, as compared with vehicle-treated disease controls and normal controls. Staining of renal tissues for (A) CD4+ T cells. (B) Scoring of stained cells in the glomerulus and periglomeruli. Original magnification, 400×. *$p<0.05$, $p<0.01$, *$p<0.005$, #Not detectable.
Figure 7:
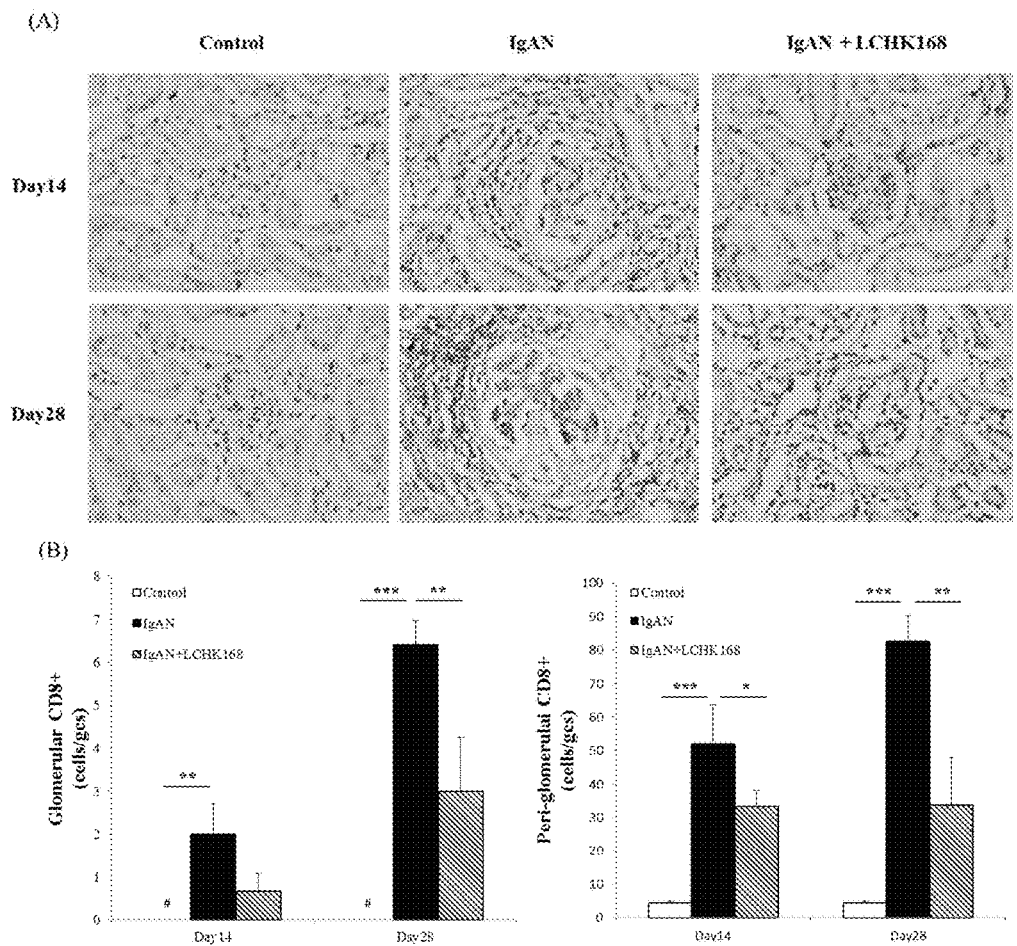
FIG. 7 shows the effects of LCHK168 on Tc cell infiltration. In mice with IgAN treated with LCHK168, as compared with vehicle-treated disease controls and normal controls. Staining of renal tissues for (A) CD8+ T cells. (B) Scoring of stained cells in the glomerulus and periglomeruli. Original magnification, 400×. *$p<0.05$, $p<0.01$, *$p<0.005$, #Not detectable.
Figure 8:
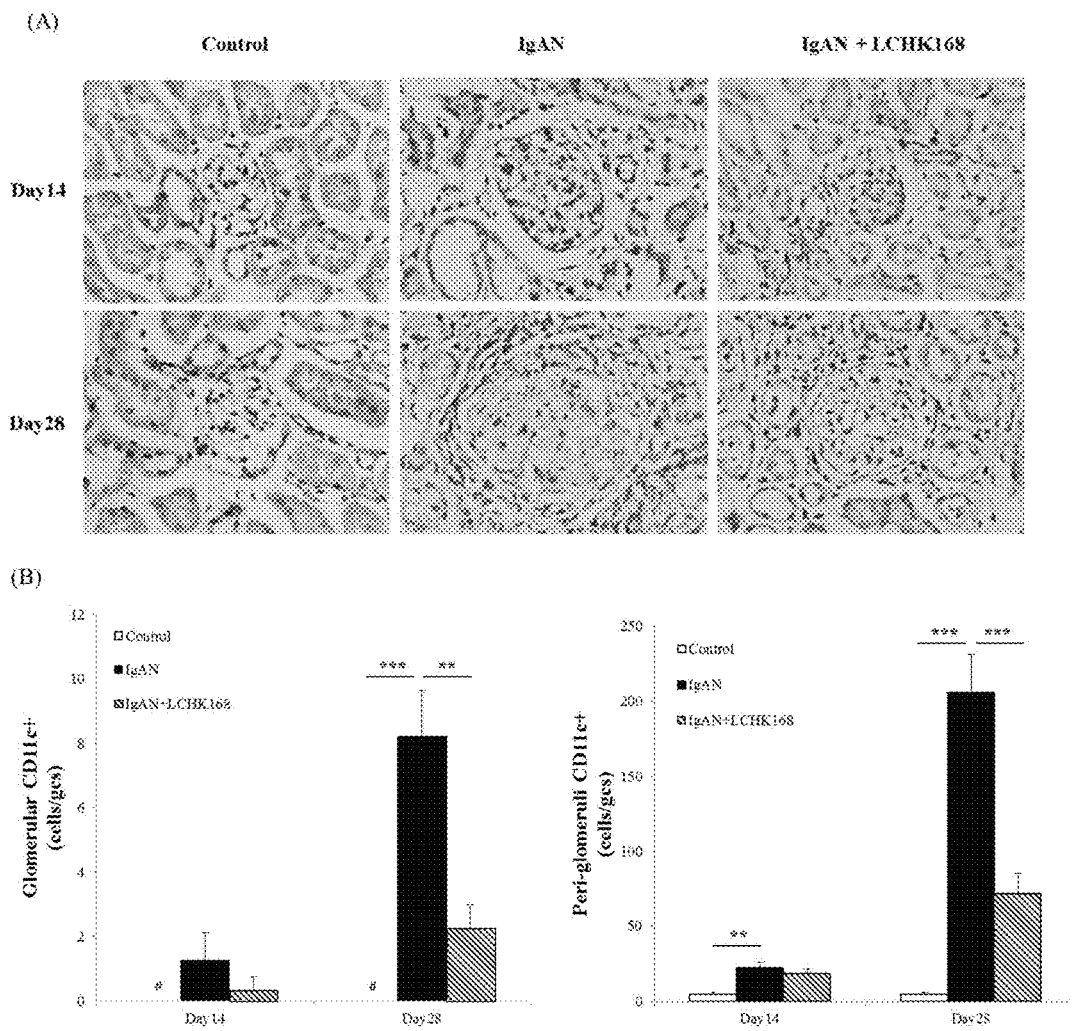
FIG. 8 shows the effects of LCHK168 on dendritic cells infiltration. In mice with IgAN treated with LCHK168, as compared with vehicle-treated disease controls and normal controls. Staining of renal tissues for (A) CD11c+ T cells. (B) Scoring of stained cells in the glomerulus and periglomeruli. Original magnification, 400×. $p<0.01$, *$p<0.005$, #Not detectable.
Figure 9:
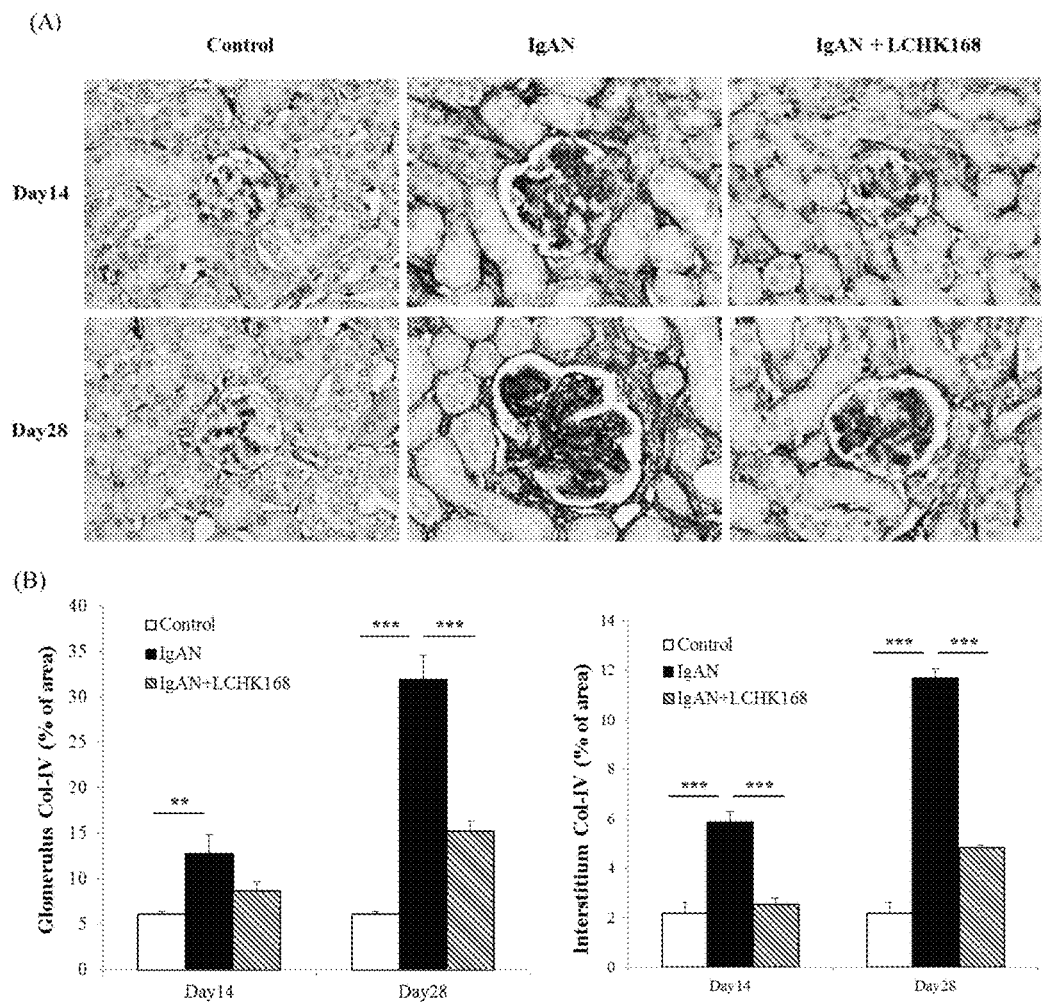
FIG. 9 shows the effects of LCHK168 renal fibrosis-related gene expression. In mice with IgAN treated with LCHK168, as compared with vehicle-treated disease controls and normal controls. (A) Collagen IV were detected by immunohistochemical staining of the kidney tissue at day 14 and 28 of treatment. (B) Scoring of stained cells in the glomerulus and periglomeruli. Original magnification, 400×. $p<0.01$, *$p<0.005$.

Furthermore, we performed IHC to evaluate the phenotypes and distribution of mononuclear leukocytes that infiltrated the kidney in the mice. Focal, but intense, staining for $CD3^+$ T cells (FIG. 4), $F4/80^+$ monocytes/macrophages (FIG. 5), $CD4^+$ T cells (FIG. 6), $CD8^+$ T cells (FIG. 7), $CD11c^+$ dendritic cells (FIG. 8) and Collagen IV (FIG. 9) was seen in the renal interstitial tissue, mostly in a periglomerular pattern, in disease control mice on day 28 compared to normal controls, although only very few inflammatory cells and fibrosis were seen in the kidney on day 14. In contrast, IgAN+LCHK168 mice showed significantly decreased infiltration of these inflammatory cells and fibrosis in the kidney compared to disease control mice on day 28 ($*p<0.05$, $p<0.01$, $*p<0.005$).

2.4 Inhibition of ROS Production with LCHK168

Figure 10:
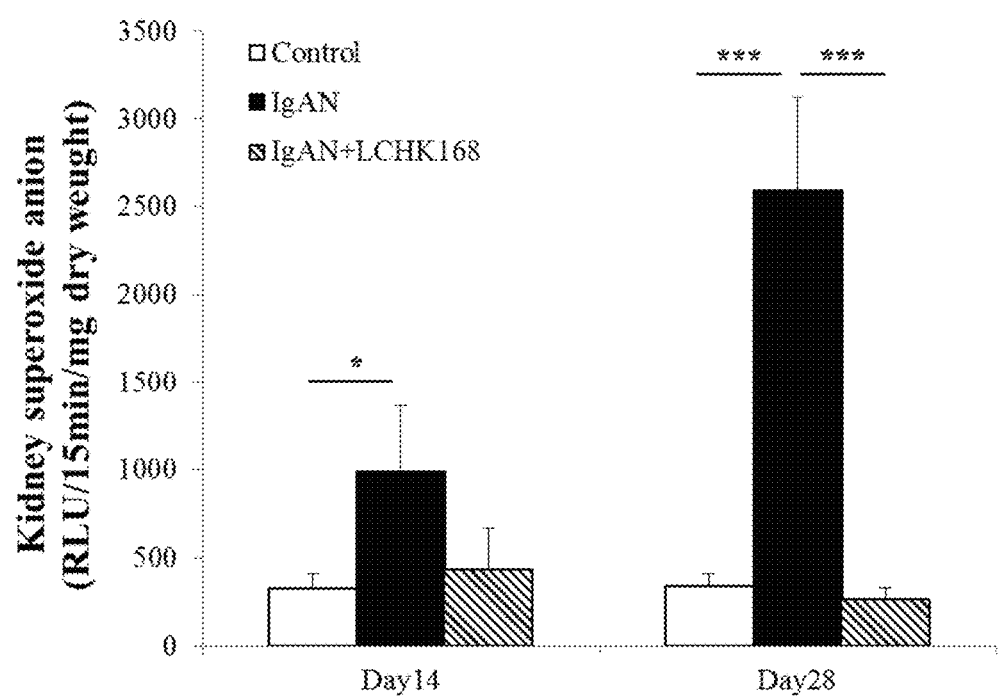
FIG. 10 shows that LCHK168 protects against reactive oxygen species (ROS) production in the kidneys of mice with IgA nephropathy (IgAN). Tissue from the kidneys of mice with IgAN treated with LCHK168, as compared with vehicle-treated disease controls and normal controls, were evaluated at day 14 and 28 of treatment for superoxide anion levels (assessed as reactive luminescence units [RLU]/15 minutes/mg dry weight). *$p<0.05$, ***$p<0.005$.

ROS are considered a major detrimental factor leading to acceleration and progression in various types of renal disorders, including IgAN. We therefore measured ROS levels systemically in renal tissues. Disease control mice showed elevated ROS levels in renal tissues (FIG. 10) on day 28 compared to normal controls. LCHK168 administration greatly inhibited the increase in renal tissues ROS levels on day 14 and substantially inhibited the increase in ROS levels in renal tissues on day 28 compared to disease control mice ($*p<0.05$, $***p<0.005$).

2.5 Modulation of Systemic Immunity with LCHK168

Figure 11:
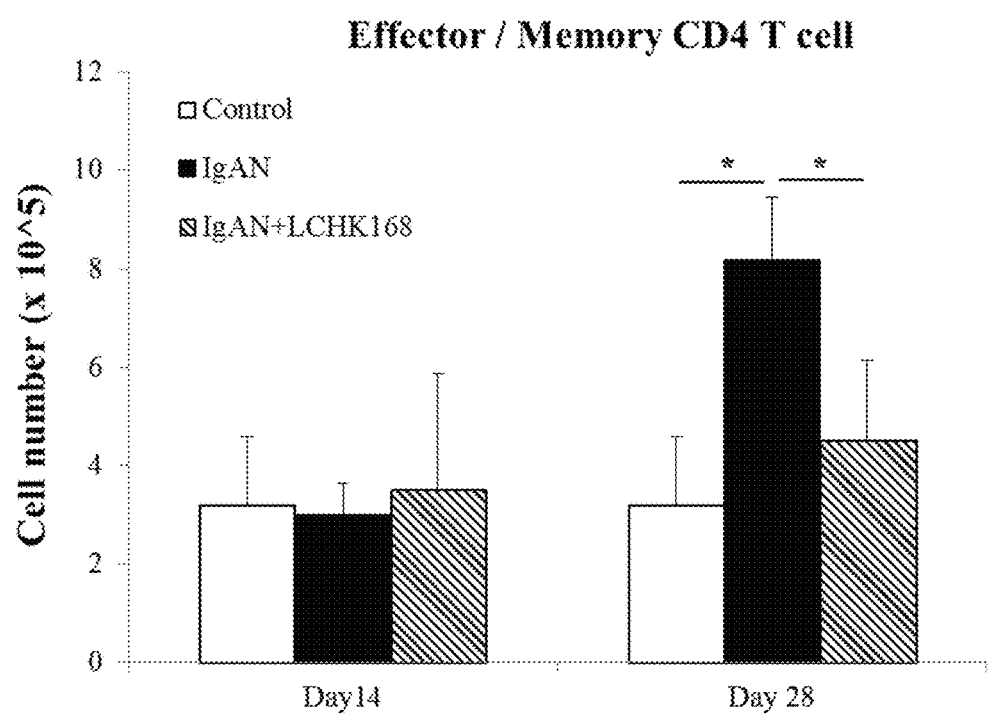
FIG. 11 shows the Flow cytometry analysis treatment with LCHK168 modulates cellular immunity in mice with IgA nephropathy (IgAN). In mice with IgAN treated with LCHK168, as compared with vehicle-treated disease controls and normal controls, the immune response at day 14 and 28 of treatment was assessed as the extent of memory $CD4^+$ T cell activation. *$p<0.05$.

Because cell-mediated immunity has long been implicated in the pathogenesis of IgAN, we examined T cell activation in splenocytes by flow cytometry. As shown in FIG. 11, an obvious increase memory $CD4^+$ T cells was observed in disease control mice compared to normal controls. LCHK168 administration induced a significant reduction memory $CD4^+$ T cells compared to disease control mice. ($*p<0.05$).

2.6 Inhibition of TLR2 Expression with LCHK168

Figure 12:
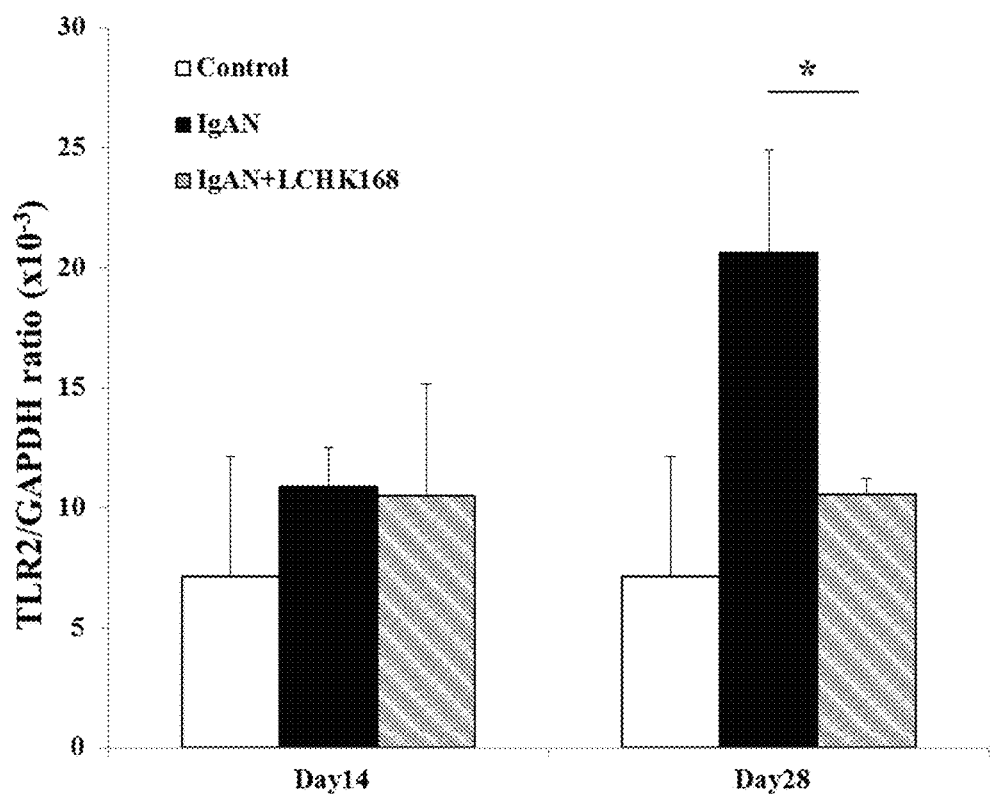
FIG. 12 shows that the treatment with LCHK168 reduces renal TLR2 mRNA levels in IgA nephropathy (IgAN). In mice with IgAN treated with LCHK168, as compared with vehicle-treated disease controls and normal controls, the mRNA levels of TLR2 (relative to GAPDH) were determined by real-time reverse transcription-polymerase chain reaction of the kidney tissue. *$p<0.05$.

Investigators have demonstrated that expression levels of TLR2 are correlated with the renal inflammation and fibrosis in IgAN. We therefore measured TLR2 mRNA levels in the kidney by real-time RT-PCR (FIG. 12). Compared to IgAN control mice, which showed significantly increased TLR2 mRNA levels at 28 days, mice in the IgAN+LCHK168 group had significantly lower TLR2 mRNA levels, although the difference at 14 days was not statistically significant. ($*p<0.05$)

2.7 Inhibition of DCs Maturation with LCHK168

Figure 13:
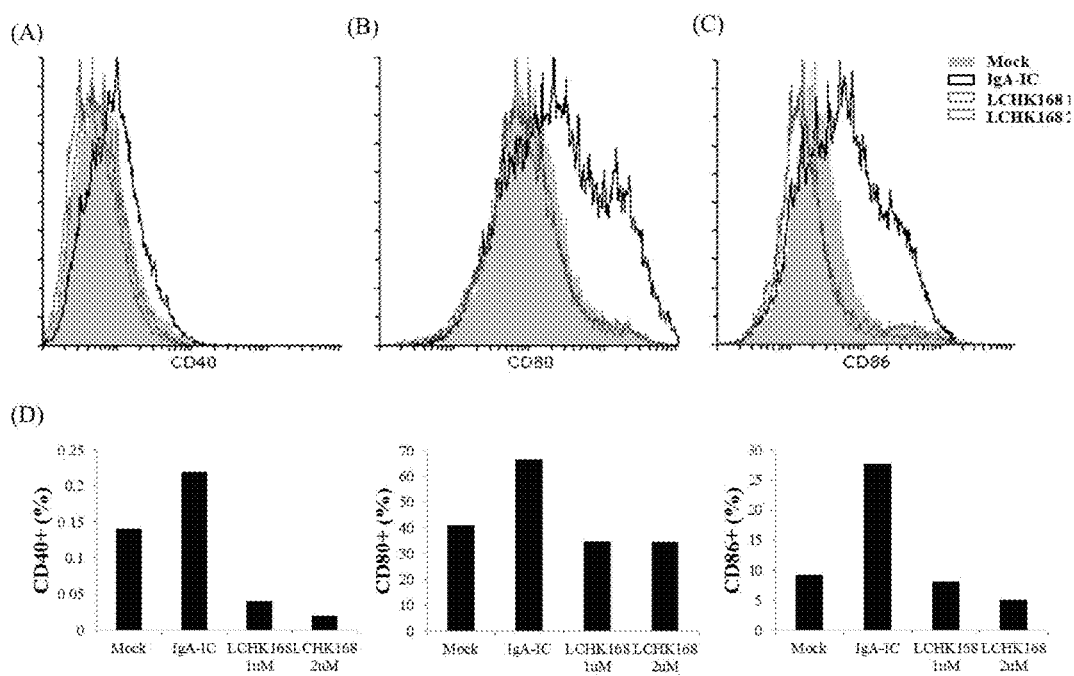
FIG. 13 shows that LCHK168 attenuated the IgA-immune complex (IgA-IC) DCs maturation. In DCs with IgA-IC treated with LCHK168, as compared with IgA-IC and mock, the expression levels of (A) CD40; (B) CD80; and (C) CD86 were determined by flow cytometry. (D) The percentage of the cell population with CD40, CD80 and CD86 dendritic cells.
Figure 14:
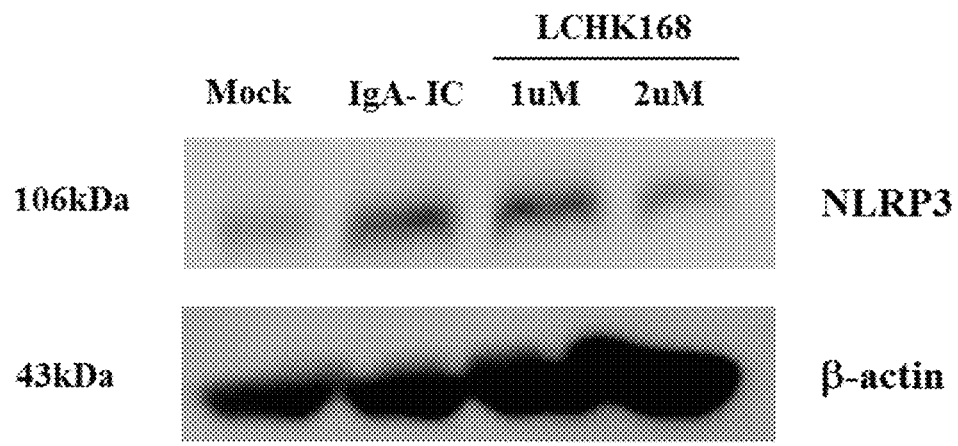
FIG. 14 shows that the activation of NLRP3 in IgA-IC stimulated DCs was reduced by LCHK168. In DCs with IgA-IC treated with LCHK168, as compared with IgA-IC and mock. Representative Western blots for (A) NLRP3 with β-actin as the loading control and (B) semiquantitative analysis for NLRP3.
Figure 14:
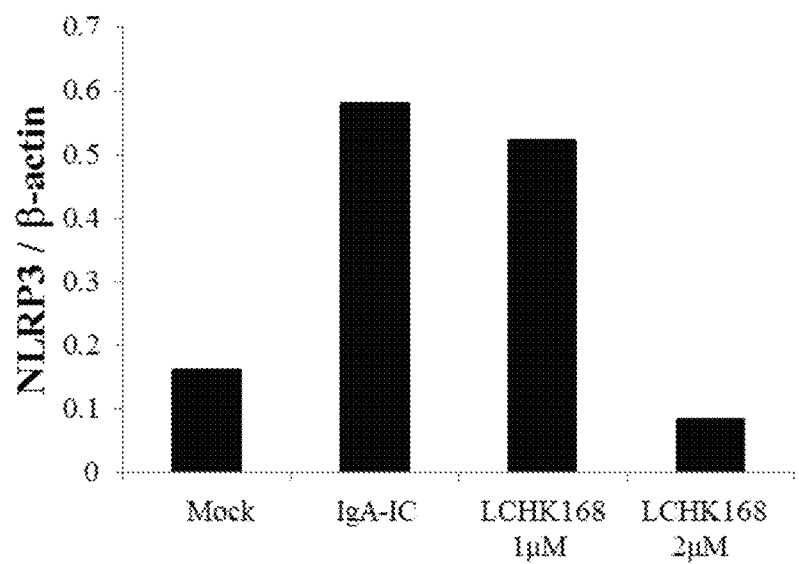

Maturation is the key step in the DC-mediated regulation of immune responses. To investigate the effect of LCHK168 on DCs maturation, we examined the expression levels of CD40, CD80, and CD86 in DCs by flow cytometry. And detected NLRP3 inflammasome expression by Western blot. IgA-IC stimulation compared to mock enhanced the expression of CD40, CD80, and CD86 in DCs. In contrast, LCHK168 treatment significantly lowered the expression levels of these molecules (FIG. 13). Moreover, DCs treated with LCHK168 showed significantly decreased NLRP3 protein expression (FIG. 14).

In summary, our study shows that ginsenoside M1 is effective in treating IgAN and preventing development of IgAN. In particular, the results shows (1) reduction of renal histopathologic features, (2) prevention of T cell and monocyte/macrophage infiltration, (3) prevention of fibrosis and collage deposition in renal interstitial tissues, (4) inhibition of production of reactive oxygen species, (5) reduction of systemic memory CD4+ T cells, (6) inhibition of dendritic cells' maturation, and (7) inhibition of NLRP3 inflammasome expression, by treatment with ginsenoside M1. All these findings suggest that ginsenoside M can be further developed to a candidate new drug for treatment or prevention of IgAN.

It is believed that a person of ordinary knowledge in the art where the present invention belongs can utilize the present invention to its broadest scope based on the descriptions herein with no need of further illustration. Therefore, the descriptions and claims as provided should be understood as of demonstrative purpose instead of limitative in any way to the scope of the present invention.

REFERENCE

1. D'Amico G. The commonest glomerulonephritis in the world: IgA nephropathy. *Q J Med.* 1987 September; 64(245):709-27.
2. Julian B A, Waldo F B, Rifai A, Mestecky J. IgA nephropathy, the most common glomerulonephritis worldwide. A neglected disease in the United States? *Am J Med.* 1988 January; 84(1): 129-32.
3. Berger J, Hinglais N. Intercapillary deposits of IgA-IgG. *J Urol Nephrol* (Paris). 1968 September; 74(9):694-5.
4. Ish M, Sar A, Lee D, Yilmaz S, Benediktsson H, Manns B, Hemmelgarn B. Histopathologic features aid in predicting risk for progression of IgA nephropathy. *Clin J Am Soc Nephrol.* 2010 March; 5(3):425-30.
5. Fujimi-Hayashida A, Ueda S, Yamagishi S, Kaida Y, Ando R, Nakayama Y, Fukami K, Okuda S. Association of asymmetric dimethylarginine with severity of kidney injury and decline in kidney function in IgA nephropathy. *Am J Nephrol.* 2011; 33(1):1-6
6. Coppo R, Camilla R, Amore A, Peruzzi L. Oxidative stress in IgA nephropathy. *Nephron Clin Pract.* 2010; 116(3):c196-8, discussion c199.
7. Lai K N, Chan L Y, Guo H, Tang S C, Leung J C. Additive effect of PPAR-γ agonist and ARB in treatment of experimental IgA nephropathy. *Pediatr Nephrol.* 2011 February; 26(2):257-66.
8. Ohashi N[1], Katsurada A, Miyata K, Satou R, Saito T, Urushihara M, Kobori H. Role of activated intrarenal reactive oxygen species and renin-angiotensin system in IgA nephropathy model mice. *Clin Exp Pharmacol Physiol.* 2009 August; 36(8):750-5.
9. Katafuchi R, Ikeda K, Mizumasa T, Tanaka H, Ando T, Yanase T, Masutani K, Kubo M, Fujimi S. Controlled, prospective trial of steroid treatment in IgA nephropathy: a limitation of low-dose prednisolone therapy. *Am J Kidney Dis.* 2003 May; 41 (5): 972-83.
10. Pozzi C, Bolasco P G, Fogazzi G B, Andrulli S, Altieri P, Ponticelli C, Locatelli F. Corticosteroids in IgA nephropathy: a randomised controlled trial. *Lancet.* 1999 Mar. 13; 353(9156):883-7.
11. Shoji T, Nakanishi I, Suzuki A, Hayashi T, Togawa M, Okada N, Imai E, Hari M, Tsubakihara Y. Early treatment with corticosteroids ameliorates proteinuria, proliferative lesions, and mesangial phenotypic modulation in adult diffuse proliferative IgA nephropathy. *Am J Kidney Dis.* 2000 February; 35(2):194-201.
12. Wakabyashi, C., Hasegawa, H., Murata, J. et al. The expression of in vivo anti-metastatic effect of ginseng protopanaxatriol saponins is mediated by their intestinal bacterial metabolites after oral administration. *J Trad. Med.,* 1997, (14): 180-185
13. Suda, K., Murakami, K., Murata, J., et al. An intestinal bacterial metabolite of ginseng protopanaxdiol saponins inhibits tumor-induced neovascularization. *J. Trad. Med.,* 2000, (17):144-150
14. Chao T K, Rifai A, Ka S M, Yang S M, Shui H A, Lin Y F, Sytwu H K, Lee W H, Kung J T, Chen A. The endogenous immune response modulates the course of IgA-immune complex mediated nephropathy. *Kidney Int.* 2006 July; 70(2):283-97.

of IgAN selected from the group consisting of (1) in the glomerulus: intrinsic cell proliferation including mesangial cell proliferation, crescent formation, neutrophil infiltration and segmental sclerosis; and (2) in the tubulointerstitial compartment: interstitial (especially peri-glomerular) mononuclear leukocyte inflammation, fibrosis, and tubular atrophy with proteinaceous casts, in the subject.

3. The method of claim 1, wherein the method of treating is effective in reducing reactive oxygen species (ROS) levels, reducing systemic memory CD4+ T cells, inhibiting dendritic cells' maturation and/or inhibiting NLRP3 inflammasome expression, in renal tissues in the subject.

4. The method of claim 1, wherein the method of treating is effective in reducing proteinuria or hematuria or lowering serum urea nitrogen level or serum creatinine level in the subject.

We claim:

1. A method of treating IgA nephropathy (IgAN) in a subject in need comprising administering to the subject an amount of ginsenoside M1 effective to treat the subject.

2. The method of claim 1, wherein the method of treating is effective in reducing or alleviating one or more symptoms 5. The method of claim 1, wherein the ginsenoside M1 is administered by parenteral or enteral route.

6. The method of claim 1, wherein the ginsenoside M1 is administered in combination with one or more therapeutic agents for treating IgAN, selected from the group consisting of corticosteroids, non-steriodal anti-inflammatory drugs (NSAIDs), cytotoxic drugs, immunosuppressants, and vasodilators.

\* \* \* \* \*

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: TLR 2 primer 1

<400> SEQUENCE: 1
gtctctgcga cctagaagtg ga                                              22

<210> SEQ ID NO 2
<211> LENGTH: 22
<212> TYPE: DNA
<213> ORGANISM: Artificial Sequence
<220> FEATURE:
<223> OTHER INFORMATION: TLR2 primer 2

<400> SEQUENCE: 2
cggagggaat agaggtgaaa ga                                              22

<210> SEQ ID NO 3
<211> LENGTH: 19
<212> TYPE: DNA
<213> ORGANISM: Artificial Sequence
<220> FEATURE:
<223> OTHER INFORMATION: GAPDH primer 1

<400> SEQUENCE: 3
tccgcccctt ctgccgatg                                                  19

<210> SEQ ID NO 4
<211> LENGTH: 20
<212> TYPE: DNA
<213> ORGANISM: Artificial Sequence
<220> FEATURE:
<223> OTHER INFORMATION: GAPDH primer 2

<400> SEQUENCE: 4
acggaaggcc atgccagtga                                                 20
```